Figure 1B:
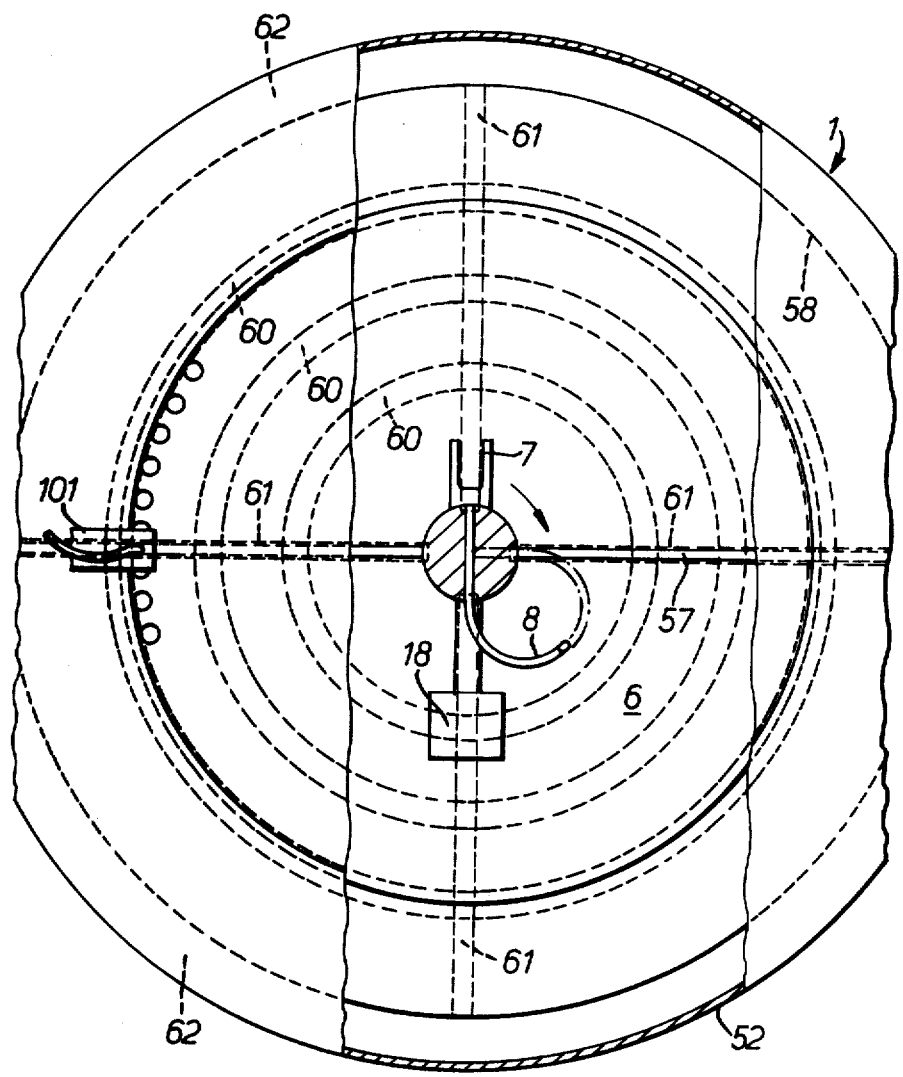

United States Patent [19]

Duff

[11] 4,054,416
[45] Oct. 18, 1977

[54] APPARATUS FOR USE IN INVESTIGATING SPECIMENS

[75] Inventor: Ian David Duff, New York, N.Y.

[73] Assignee: Secretary of State for Social Services, London, England

[21] Appl. No.: 714,677

[22] Filed: Aug. 11, 1976

[51] Int. Cl.² .................... F27D 11/00; B01L 7/02; B01L 9/06; G01N 1/10
[52] U.S. Cl. ........................ 23/259; 23/292; 219/413; 219/428; 219/530; 236/3; 237/3
[58] Field of Search ................ 23/259, 253, 292; 219/413, 428, 530; 236/3; 237/3

[56] References Cited
U.S. PATENT DOCUMENTS

| 3,399,116 | 8/1968 | Du Bois et al. | 23/292 X |
| 3,457,048 | 7/1969 | Stephens et al. | 23/259 X |
| 3,622,047 | 11/1971 | Oberli | 23/259 |
| 3,811,842 | 5/1974 | Diebler et al. | 23/259 |

Primary Examiner—R.E. Serwin
Attorney, Agent, or Firm—Reed, Smith, Shaw & McClay

[57] ABSTRACT

The apparatus comprises a turntable carrying, in a circular array centered on a central rotational axis of the turntable, a plurality of vials extending below the underside of the turntable. A stepper motor imparts stepwise rotational motion to the turntable so that during dwell periods of the turntable, specimens in the vials can be investigated optically.

Air in a space below the turntable and bounded laterally and at the bottom by an enclosure is circulated by a rotating vane, and a thermistor, responsive to the temperature in the region of the vials, controls a heater in the space below the turntable so as to maintain the temperature of the vials substantially at a predetermined value.

In order to dispense liquids into the vessels at predetermined temperatures, the apparatus additionally includes a liquid dispenser mounted adjacent the turntable and comprising a tubular body with an electric heating coil and a dispensing device which dispenses liquid from the outlet of the tubular body in predetermined quantities, the heating coil being supplied with the necessary quantity of power to maintain the temperature of the dispensed liquid substantially at a predetermined value.

Preferably, the apparatus is used for analysing blood specimens.

6 Claims, 5 Drawing Figures

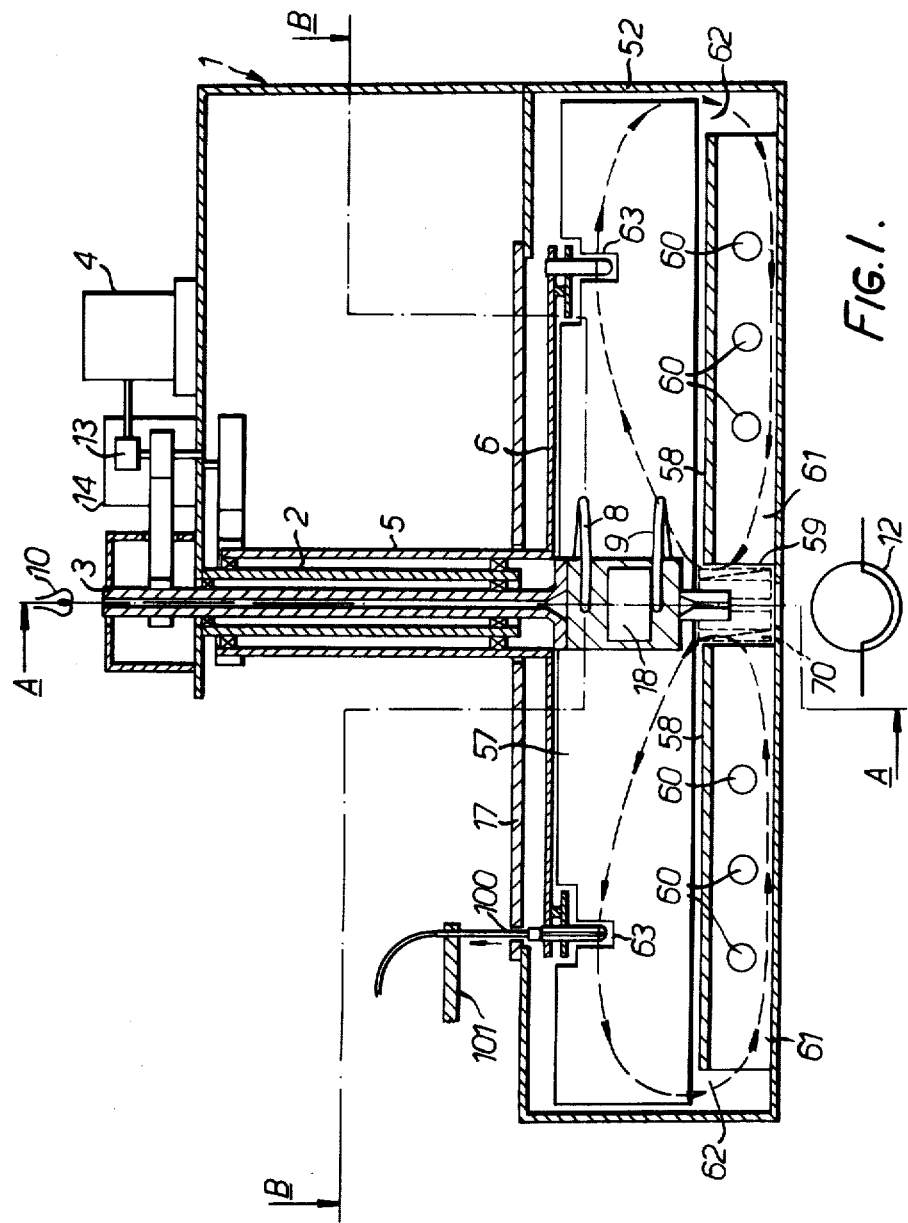

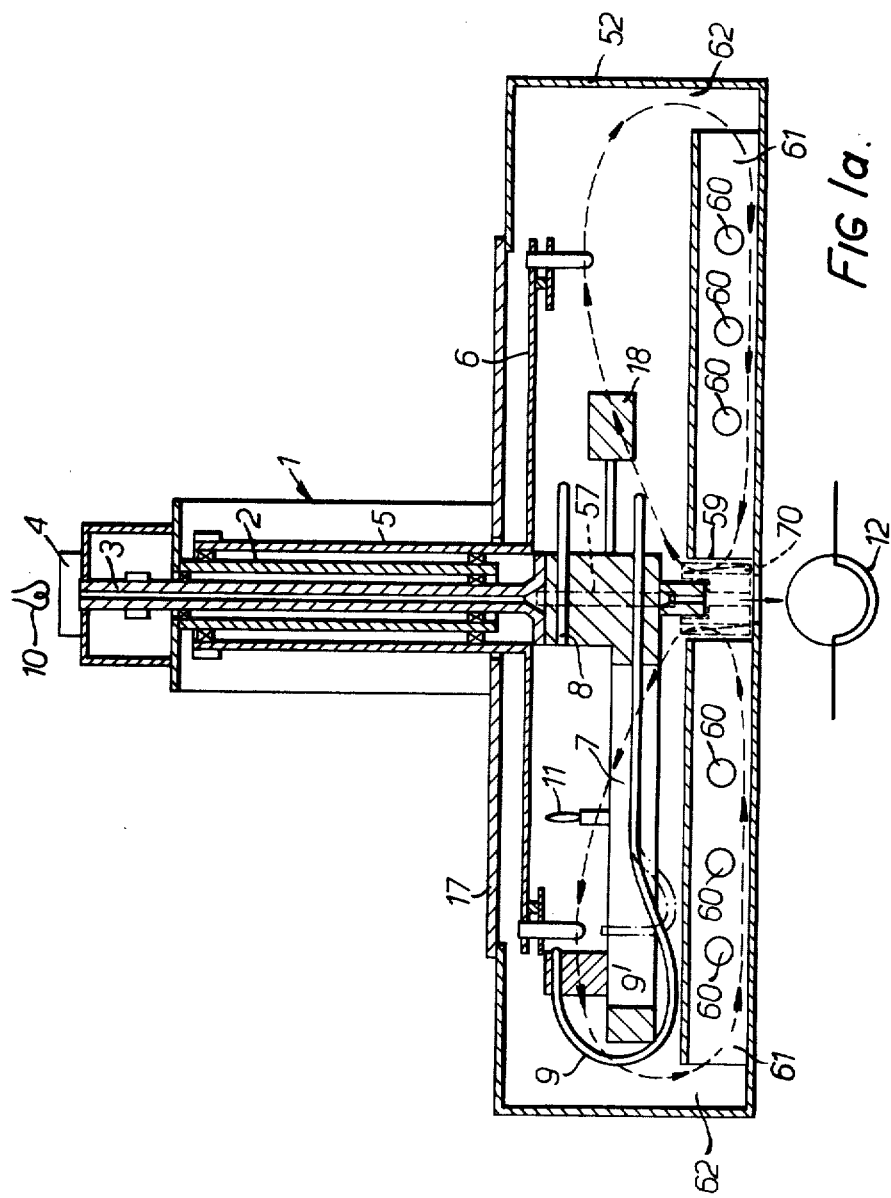

APPARATUS FOR USE IN INVESTIGATING SPECIMENS

This invention relates to apparatus for use in investigating specimens.

U.S. patent application Ser. No. 695,032, filed on the June 11, 1976 in the name of Roger Abraham Bunce, relates to apparatus for use in investigating specimens, comprising a substantially horizontal turntable having a central rotational axis and being adapted to support, in a circular array centred on the said rotational axis, a plurality of vessels, each for containing a specimen to be investigated, the apparatus further comprising means for advancing the turntable stepwise about the said rotational axis so that, during dwell periods of the turntable, specimens may be investigated, the turntable being adapted to support the vessels in such manner that they extend downwardly below the underside of the turntable.

The aforesaid U.S. Patent Application is concerned with the problem of obtaining high accuracy of analysis of specimens in the vessels of such apparatus, and recognises that a contributory factor to achieving the desired high accuracy is ensuring that the temperature of the vessels is maintained at a predetermined value to within close limits. To this end, in the specimen investigation apparatus of the aforesaid application there is a space bounded, laterally and at the bottom, by an enclosure and limited upwardly by the turntable so that when the vessels are in position, supported by the turntable, they extend into the said space, and wherein there are means provided for changing the temperature of air in said space and means positioned within said space and arranged to circulate air between the temperature changing means and the vessels wholly within said space, the temperature changing means being provided with a control device for maintaining the temperature of the said vessels substantially at a predetermined value. Hereinafter, such apparatus will be termed "apparatus as specified".

The present invention represents an improvement in apparatus as specified and is concerned with taking further measures to control closely the temperature of the specimens provided in the vessels.

According to the invention, there is provided apparatus as specified, comprising a liquid dispenser mounted adjacent the turntable and operable to dispense liquid into a vessel when in position on the turntable, the dispenser comprising a tubular body having an inlet, for receiving liquid to be dispensed, and an outlet comprising a dispensing tip for dispensing the received liquid, the dispenser being provided with means for dispensing the liquid in predetermined quantities and the dispenser also comprising temperature control means which is so arranged that, in use, the temperature of the liquid being dispensed is maintained substantially at a predetermined value.

Preferably, the temperature control means comprise a heating coil, wound around the tubular body to extend substantially over its length, and a thermistor, positioned is a cavity in a portion of the tubular body alongside the dispensing tip and arranged to control operation of the heating coil. Generally, the tubular body consists of copper and the heating coil is surrounded by a heat insulative jacket. The dispensing tip may be removable to enable replacement thereof.

In a preferred construction for the means for dispensing the liquid in predetermined quantities, it comprises a first pump operative to draw a first liquid into the dispenser, when the dispensing tip thereof is immersed in such first liquid, by removing a portion of a second liquid filling the dispenser when the apparatus is in use so as to fill the dispenser only partially with such first liquid and also operative to dispense the first liquid in the dispenser into a vessel in position on the turntable, and a second pump operative to dispense such second liquid in the dispenser into the vessel following dispensing of the first liquid.

Figure 2:
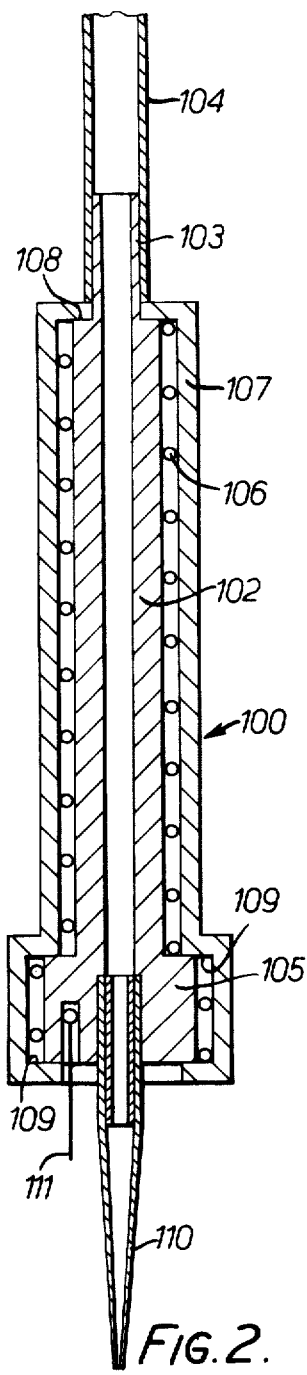
Figure 3:
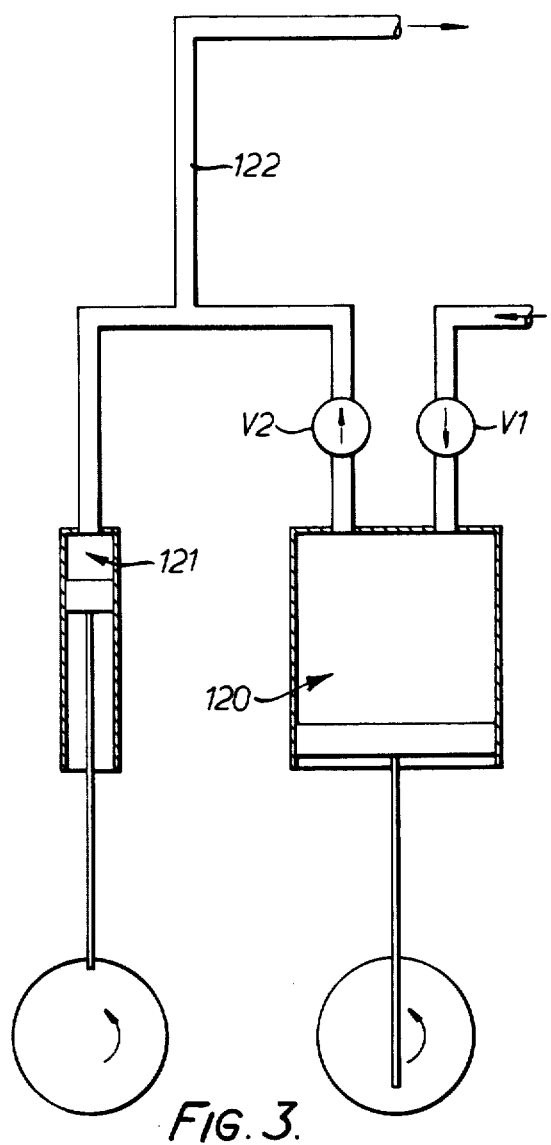

For a better understanding of the invention, and to show how the same may be carried into effect, reference will now be made, by way of example, to the accompanying drawings, in which:

FIG. 1 shows a vertical sectional view of one form of specimen investigation apparatus in the form of an automatic blood analysing machine, FIG. 1a is a sectional view of the machine taken along the line A—A of FIG. 1, FIG. 1b shows a horizontal sectional view of the machine taken on the line B—B of FIG. 1 with a cover of the machine removed, FIG. 2 is a vertical sectional view through a dispenser incorporated in the blood analysing machine, and FIG. 3 illustrates diagrammatically an arrangement whereby a predetermined quantity of a serum or reagent, followed by a predetermined quantity of diluent, is dispensed through the dispenser of FIG. 2.

The machine illustrated in FIGS. 1, 1a and 1b is used for colorimetric, light scattering and fluorimetric evaluation of reactions between samples of blood and reagent(s), and comprises a stationary frame 1 which carries a hollow vertical trunnion 2. Extending coaxially inside the trunnion 2 is a hollow rotatable shaft 3 which is connected at its upper end by a pulley and belt arrangement and a gearbox 13 to an electric motor 4 mounted on the frame 1. The trunnion 2 is surrounded coaxially by a further rotatable shaft 5 which carries a horizontal turntable 6 at its lower end and is connected at its upper end by a further pulley and belt arrangement to a second electric motor 14, which is a stepping motor.

The turntable 6, which is covered by a stationary cover 17, is circular, its centre being on the common axis of the trunnion 2 and the shafts 3 and 5, and has about its periphery a plurality of equally spaced vials. These vials are removably fitted into notches in the turntable.

The lower part of the frame 1 is in the form of a cylindrical enclosure 52 having an inwardly projecting annular flange on the radially innermost portion of which the cover 7 is positioned. Each vial extends downwardly from the level of the turntable into the space bounded laterally and at the bottom by the enclosure and limited upwardly by the turntable 6. As can be seen in FIGS. 1 and 1a, the diameter of the turntable is slightly greater than the diameter of the opening in the top of the enclosure 52 and the turntable is arranged within the enclosure at a very small spacing below the flange of the enclosure. In this way, the transport of air between the exterior of the enclosure and its interior and vice versa is minimal.

The shaft 3 is connected at its lower end, which is below the table 6, to a horizontal arm 7 which extends radially with respect to the shaft 3. The shaft 3 is also connected to a counterbalance 18 for the arm 7. The arm 7 carries two fibre optic light guides 8 and 9. The light guide 8 has an input end at the upper end of the shaft 3 and extends vertically downwards coaxially within the shaft 3. At the lower end of the shaft 3 the guide 8 extends therefrom radially outwardly along the arm 7 and has an output end at a position along the arm which is inward of the periphery of the table 6. The output end of the guide 8 defines a slit-form output aperture. The guide 9 has an input end which is mounted on the arm 7 outward of the periphery of the table and aligned with the end of the guide 8. The input end of the guide 9 defines a slit-form input aperture. The guide 9 extends from the periphery of the table radially inwards along the arm 7 and has an output end which is directed vertically downwards along the axis of the shaft 3. FIG. 1b shows how the light guide 8 is looped between its radial and axial portions in order to avoid imposing excessive curvature on the guide. The arrangement of the guide 9 (not shown in FIG. 1b) is the same.

Above the upper end of the shaft 3 is a lamp 10 arranged to direct light vertically downwards into a circular input aperture defined by the input end of the light guide 8. Between the lamp 10 and the input aperture may be mounted a filter or grating unit for selecting the wavelength of light entering the input aperture and thereby enabling different reactions to be evaluated. Radially outwardly of the output end of the guide 8 is an optical system comprising a correction slit (not shown), converging lens 11 and a further correction slit (not shown), for focusing light delivered by the guide 8 on liquid in a vial. The optical system is clamped to a horizontal slideway, formed in the arm 7, to facilitate adjustment. Light which is transmitted by the liquid is received by the guide 9 at its input end and is delivered to its output end from which it is directed vertically downwards, along the axis of the shaft 3, to a photomultiplier 12.

The shaft 3 is also connected at its lower end to a vane 57 arranged within the space bounded by the enclosure and turntable and spaced angularly from the arm 7, about the vertical axis of rotation of the shaft 3, by 90°. The vane consists essentially of two rectangular plates which are arranged so that the longer and shorter edges of the rectangular faces of the plates are respectively radially and axially disposed relative to the shaft 3. The vane is formed with cut-out portions 63 which are slightly larger than, but conform approximately to the shape of, the vials. This enables the vane 7 to be rotated with its upper edge close to the underside of the turntable while at the same time ensuring that rotation of the vane is not impeded by the vials. In addition, the overall length end-to-end of the vane is only slightly less than the internal diameter of the peripheral wall of the enclosure.

Arranged beneath the vane on radial supporting plates 61 and with a small spacing from the vane is a horizontal annular plate 58 whose central opening 59 is coaxial with the shafts 5 and 6 and whose greater diameter is less than the length of the vane 4 from end-to-end in order to leave an annular air gap 62 between the outer edge of the annular plate 58 and the peripheral wall of the enclosure. Electric heaters 60, arranged in the form of concentric rings, are positioned in the space between the base of the enclosure and the plate 8 and extend through openings in the supporting plates 61. A thermistor (not shown), positioned within the enclosure close to the vials and responsive to the temperature within the space limited by the plate 58, turntable 6 and peripheral wall of the enclosure, is arranged to control the power supplied to the heaters 10 and thereby regulate the quantity of heat generated by the heaters so as to maintain the temperature within the space, and thereby that of the vials, at a predetermined value.

Dispensing means are provided on the flange of the enclosure 52 adjacent the periphery of the turntable 6 whereby, at a first station, a predetermined quantity of blood, together with a predetermined quantity of diluent, is dispensed into a vial when the turntable is at rest between stepwise rotational advancements and, at a second station, when the turntable is again at rest, predetermined quantities of reagent and diluent are dispensed into a vial containing blood and diluent from the first station. For this purpose a dispenser 100, to be described in detail hereinbelow with reference to FIG. 2, is provided at each station. The dispenser is mounted on a support member 101 and is vertically displaceable to allow itself to be raised clear of the vial so that the turntable can undergo its stepwise rotational advancement. The support member 101 can be swung to one side to guide the probe over a container of blood or reagent. The dispenser is lowered into the container and a measured quantity of blood or reagent is drawn in. When the turntable next comes to rest, the dispenser is returned to its lowered position in another vial and the measured quantity is dispensed, followed by a measured quantity of diluent, into the vial.

When the blood analysing machine is in operation, the turntable 6 is rotated stepwise by the motor 14 past the dispensing means, whereat a sample of blood and a quantity of reagent (and possibly also diluent and/or dye) is placed in a different vial, as has just been explained, during each dwell period of the turntable 6 between successive stepwise rotational advancements of the table. At the same time, the motor 14 is caused to rotate the shaft 3 through at least one revolution during each dwell period, thus causing the arm 7 to rotate so that the light beam from the light guide 8 scans the vials in succession and the light transmitted by the liquids in the vials is received by the light guide 9 and passed to the photomultiplier 12 which provides an output voltage, the magnitude of which depends upon the intensity of light received by the guide 9. At the same time as the vials are scanned in succession, the vane 57 rotates with the arm 7 and in doing so it sweeps out the space limited by the plate 58, the turntable 6 and the peripheral wall of the enclosure and causes the air in this space to rotate. Owing to centrifugal force, the air passes around the individual vials in the radially outward direction, downwardly through the annular air gap 62 between the plate 58 and peripheral wall of the enclosure, radially inwardly to pass around the electrical heaters 10, and then upwardly and radially outwardly again. At the same time, the air circulates about the vertical axis of the vane 57. Thus a circulating air pattern is set up as indicated in FIGS. 1 and 1a. The thermistor ensures that the vials, and thus the specimens, are maintained at a predetermined temperature to within close limits.

The air flow pattern achieved within the enclosure is very effective in reducing temperature fluctuations in the region of the vials projecting downwardly into the enclosure. In fact, following investigation, it has not been possible to measure any such temperature fluctuations but a maximum value of ± 0.05° C has been estimated. In a typical form of blood analysing machine, the thermal time constant of the machine is about 30 seconds and the maximum input power consumed is about 200 watts.

The photomultiplier 12 is connected to a computer (not shown) which stores a set of data for each revolution of the shaft 3, representing the output voltage of the photomultiplier 12 for each of the vials. When the shaft 3 is rotated at least twice during each dwell period, the computer uses the several sets of data to form a mean value for the output voltage of the photomultiplier in respect of each vial. In practice, it is more convenient to rotate the motor 4 continuously rather than for it to rotate only during each dwell period of the turntable 6. Then, the computer is arranged so as to disregard the data received during each stepwise rotational advancement of the turntable 6 between successive dwell periods. Furthermore, the computer 4 is so arranged that if during each dwell period the shaft 3 rotates through a non-integral number of revolutions the computer accepts data only for the nearest integral number of revolutions of the shaft, below the actual number of revolutions undergone.

In the circumstances, therefore, the illustrated machine is used for colorimetric analysis of the blood samples. By making a slight modification, however, the machine may be used for light scattering or fluorimetric analysis of the blood samples. The modification is shown in broken lines in FIG. 1 and entails replacing the light guide 9 by a guide 9' whose input end is vertically below the vial and perpendicular to the output end of the guide 8 and placing a colour filter between the output end of the light guide 9' and the photomultiplier 12. Then the output voltage of the photomultiplier depends upon the intensity with which light from the guide 8 is a selected wavelength band, predetermined by the filter, leaves the vial.

Referring to FIG. 2, the dispenser 100 will now be described. It comprises an upright tubular body 102 of metal having at its upper part an inlet connection stub 103 to which a flexible inlet pipe 104 for liquid supplied to the dispenser is connected.

A heating coil 106 is wound around the tubular body to extend substantially over its length. The heating coil is in turn surrounded by cylindrical jacket 107 of heat insulative material which seats at its upper end against an annular shoulder 108 of the tubular member and of which two opposite annular surfaces 109 engage with a collar 105 formed at the lower end of the tube.

The tubular body 102 is formed in the collar 105 at the lower end of the tube with a bore which is concentric with the axis of the tubular body and of slightly larger diameter than the internal diameter of the body. Into the bore is fitted a replaceable dispensing tip 110 that may have a stainless steel insert to reduce the volume of the space provided within the dispensing tip and not heated. The tip 110 projects downwardly beyond the lower end of the tubular member and heat insulative jacket 107. The collar 105 is formed with a cavity to receive a thermistor 111 which is arranged to control the quantity of current supplied to the electrical heating coil so as to maintain the dispensed liquid substantially at a predetermined temperature.

In operation, a dispenser 100 is provided at a first dispensing station at which a sample of unheated serum together with a quantity of heated diluent is placed into a single vial during one dwell period of the turntable between successive stepwise rotational advancements of the turntable. This is achieved by sucking into the dispenser filled with diluent a quantity of serum which is sufficiently small that it is contained entirely within the dispensing tip, and then dispesing the diluent and serum. Simultaneously, a second dispenser 100 at a second station places a quantity of heated reagent together with a quantity of heated diluent into another vial. The procedure is much the same as in the case of the first station except that a sufficiently large quantity of reagent is sucked in to fill the dispensing tip completely and partially fill the tube so that the reagent becomes heated too. The position of the latter vial with respect to the first one is chosen such that the stepwise advancements of the turntable cause each vial to move from the serum/diluent dispenser to the reagent/diluent dispenser. To dispense the liquids, each dispenser 100 is displaced downwardly until the dispensing tip 110 is positioned near to the bottom of the vial and touching one wall of the vial in order to avoid the formation of droplets at the lower end of the dispensing tip. After the liquid contents of each tube assembly have been dispensed, the dispenser is raised to its upper position in which the dispensing tip is clear of the vial and then the turntable is indexed by one step, after which the dispenser is displaced downwardly again into the next vial, and so on.

One convenient way of supplying the diluent to the dispenser and causing the serum and reagent to be sucked in and the whole contents subsequently dispensed is to use the arrangement illustrated very diagrammatically in FIG. 3 of accompanying drawings. This comprises a diluent pump 120 having an inlet supplied through a non-return valve V1 and an outlet with a non-return valve V2, and a syringe pump 121, these two pumps discharging into a common output connection 122 supplying the dispenser 100 by way of the flexible pipe 104. In operation, the pumps undergo a cycle commencing in the position shown in FIG. 3. The dispensing tip is positioned in the serum or reagent and the syringe pump 121 undergoes a half revolution to suck into the dispenser a measured quantity of serum or reagent, determined by the stroke of the pump. After the dispensing tip has been repositioned for dispensing the diluent and serum or reagent, the syringe pump 121 completes its cycle to dispense the serum or reagent and this is immediately followed by the diluent pump 120 undergoing a half revolution to dispense the heated diluent in a predetermined quantity governed by the stroke of the diluent pump. Finally, the cycle is completed by the diluent pump undergoing another half revolution to recharge its cylinder with fresh diluent.

As an example, at the serum dispensing station either 5 $\mu$l or 25 $\mu$l of serum at ambient temperature is to be mixed with preheated diluent from the dispenser to give a total volume of 150 $\mu$l. The serum and diluent are dispensed into a vial at the particular temperature determined by the thermistor controlling the heaters 60. The vial of course has a finite thermal capacity and so will affect the temperature of the liquid mixture. After one minute the reagent and diluent are added and it is not until then that an accurately controlled temperature is required. At this time the mixture of serum and diluent should be within $\pm 0.05°$ C of the temperature within the enclosure. It has been shown experimentally that this condition will be achieved providing that the diluent at the serum dispensing station is preheated to within $\pm 0.5°$ C of the required temperature, a requirement that can be satisfied using a solid copper tubular body in the dispenser.

At the reagent dispensing station, 50 μl of reagent at 4.0 ± 0.5° C is dispensed with 300 μl of preheated diluent from the dispenser into the vial. The dispenser is required to dispense every 6 seconds and so it will generally be possible to control the mean temperature of the dispensed mixture with good precision, although considerable temperature gradients may be present within the heated diluent. Experiments suggest that control to within ±0.2° C for the dispensed reagent and diluent (that includes errors caused by incorrect reagent temperature) should be possible. This would produce a maximum initial error of 0.15° C in the reaction mixture which would reduce to an error of 0.1° C within 30 seconds.

In some applications the addition of more than one reagent may be desirable. In such cases the conditions required at the additional reagent dispensing station(s) are not as stringent. They depend upon time of addition and quantity added. It should be noted that if the addition of further reagent(s) were immediately to follow dispensing of the first reagent, difficulties may be encountered since any errors would add directly to those already present, no time being allowed for correction of errors by the preheated vials.

Thus, with the blood analysing machine described, the vials are maintained at a closely controlled temperature and, in addition, so also are the serum, reagent and diluent when they are dispensed. Thus, the reactions which take place between the blood and reagent occur under precisely controlled temperatures, so that the data obtained from the blood analysing machine assists in highly accurate analysis of the blood samples.

With reference to FIGS. 1 and 1a, in a modification, a fan 70 is mounted centrally within the enclosure to extend from the lower edge of the vane 57 to the bottom of the enclosure. This fan is driven independently of the rotating arm 7 and vane 57. The purpose of the fan is to ensure some circulation of air within the enclosure even when the arm 7 and vane 57 are at rest, so as to avoid the possibility of the heaters 60 overheating owing to the thermistor controlling them being situated close to the vials.

Although the use of the arrangement described with reference to FIG. 3 to supply the dispenser 100 is preferred, it would be possible to use one dispenser for dispensing the first quantity of diluent, another for the serum, a third one for the second quantity of diluent, and a fourth dispenser for the reagent. The means for supplying each dispenser would then be required merely to supply a measured quantity of diluent, serum or reagent at the appropriate intervals of time.

I claim:

1. Apparatus for use in investigating liquid specimens comprising a substantially horizontal turntable having a central rotational axis and being adapted to support a plurality of vessels for liquid speciments in a circular array centered on the said rotational axis such that the vessels extend below the underside thereof; means for stepwise rotation of the turntable for specimen investigation during dwell periods; an enclosure disposed beneath the turntable to define a space bounded laterally and at the bottom of said enclosure and upwardly by the turntable and into which the vessels extend when positioned in the turntable; temperature changing means for changing the temperature of air in said space; air circulating means disposed in said space and arranged to circulate air between the temperature changing means and the vessels wholly within said space; a control device for the air temperature changing means arranged to maintain the temperature of the vessels substantially at a predetermined value; and a liquid dispenser mounted adjacent the turntable for dispensing liquid specimens into different vessels in the turntable during respective dwell periods thereof, the dispenser comprising a tubular body of a high thermal conductivity having an inlet through which liquid may enter said tubular body, and an outlet which comprises a dispensing tip of high thermal conductivity through which liquid may leave the tubular body, said tubular body also including a cavity adjacent said outlet, the dispenser being provided with means for charging the tubular body with liquid by way of said inlet and for dispensing predetermined quantities of such liquid, said tubular body including an electric heating coil, wound around substantially its length and a thermistor positioned in said cavity to control said heating coil to maintain the temperature of the liquid being dispensed substantially at a predetermined value.

2. Apparatus according to claim 1, wherein the tubular body consists of copper and the heating coil is surrounded by a heat insulative jacket.

3. Apparatus according to claim 1, wherein the dispensing tip is removable to enable replacement thereof.

4. Apparatus according to claim 1, wherein the said means for charging the tubular body with liquid and for dispensing the liquid in predetermined quantities comprises a first pump operative to draw a first liquid into the dispenser when the dispensing tip is immersed in such first liquid, by removing a portion of a second liquid filling the dispenser so as to fill the dispenser only partially with such first liquid and also operative to dispense the first liquid in the dispenser into a vessel in position on the turntable, and a second pump operative to dispense such second liquid in the dispenser into the vessel following dispensing of the first liquid.

5. Apparatus for use in investigating liquid specimens, comprising a substantially horizontal turntable having a central rotational axis and being adapted to support a plurality of specimen vessels in a circular array centered on the said rotational axis such that the vessels extend below the turntable; means for stepwise rotating the turntable so the specimens may be investigated during dwell periods; an enclosure disposed beneath the turntable and having an internal surface symmetrical with the rotational axis to define a space bounded laterally and at the bottom by said enclosure and upwardly by said turntable; a baffle plate disposed within the enclosure to provide between said plate and the turntable a first space into which said vessels extend when supported by the turntable, and between the said plate and the base of the said enclosure a second space, the outer edge of the baffle plate being separated by an air gap from the periphal wall of said enclosure, said baffle plate having a central hole for air to circulate between the said first and second spaces through said air gap and said central hole; a rotary vane disposed in the said first space and mounted with its axis of rotation coincident with that of the turntable, said vane having at least one cut-out portion to permit relative rotational movement between the turntable with the vessels in position thereon and the vane, said vane having a shape conforming substantially to the vertical cross-section of said first space so that the vane sweeps out a volume substantially equal to that of the said first space during rotation; air temperature changing means disposed in said second space; a control device for the air temperature changing means arranged to maintain the temperature of the vessels substantially at a predetermined value; and a liquid dispenser mounted adjacent the turntable for dispensing liquid specimens into different vessels in the turntable during respective dwell periods thereof, said dispenser comprising a tubular body of high thermal conductivity and having an inlet through which liquid may enter the tubular body and an outlet which comprises a dispensing tip of high thermal conductivity through which liquid may leave the tubular body, said tubular body including a cavity adjacent said outlet; said dispencer being provided with means for charging the tubular body with liquid by way of said inlet and for dispensing predetermined quantities of such liquid, said tubular body includes an electric heating coil wound around substantially its length, and a thermistor positioned in said cavity to control operation of the heating coil to maintain the temperature of the liquid being dispensed substantially at a predetermined value.

6. Apparatus for use in investigating liquid specimens, comprising a substantially horizontal turntable having a central rotational axis and being adapted to support a plurality of specimen vessels in a circular array centered on the said rotational axis such that the vessels extend below the turntable; means for stepwise rotating the turntable for investigating specimens; during dwell periods of the turntable an enclosure disposed beneath the turntable and having an internal surface symmetrical with the rotational axis to define a space bounded laterally and at the bottom by the enclosure and upwardly by the turntable; a baffle plate disposed within the enclosure to provide between said plate and the turntable a first space into which the vessels extend when supported by the turntable, and between said plate and the base of said enclosure a second space, the outer edge of the baffle plate being separated by an air gap from the peripheral wall of said enclosure and the baffle plate being formed with a central hole so that air can circulate between the said first and second spaces by way of the air gap and said central hole; a rotary vane disposed in the said first space and mounted with its axis of rotation coincident with that of the turntable, said vane having at least one cut-out portion to permit relative movement between the turntable with the vessels in position thereon and the vane, said vane having a shape conforming substantially to the vertical cross-sectional of said first space so that the vane sweeps a volume substantially equal to that of the said first space during rotation; and air heater disposed in said second space; a control device for the air heater including a thermistor mounted to be responsive to the temperature in the region of the vessel, the control device being arranged to control operation of the air heater to maintain the temperature of the vessels substantially at a predetermined value; fan means in said enclosure arranged to be driven independently of the vane to maintain sufficient circulation of air within said space bounded by the said enclosure and the turntable to prevent the air heater from overheating; and a liquid dispenser mounted adjacent the turntable for dispensing liquid specimens into different vessels in the turntable during respective dwell periods thereof, said dispenser comprising a tubular body of high thermal conductivity and having an inlet through which liquid may enter, and an outlet which comprises a dispensing tip of high thermal conductivity through which liquid may leave the tubular body, said tubular body including a cavity adjacent to the outlet, said dispenser having means for charging the tubular body with liquid by way of said inlet and for dispensing predetermined quantities of such liquid, said tubular body including an electric heating coil wound around substantially its length, and a thermistor positioned in said cavity to control the heating coil to maintain the temperature of the liquid being dispensed substantially at a predetermined value.

* * * * *